United States Patent [19]
Nelson

[11] 4,261,354
[45] Apr. 14, 1981

[54] INHALATOR-BREATHING APPARATUS

[76] Inventor: Byron G. Nelson, P.O. Box 6457, Lake Charles, La. 70606

[21] Appl. No.: 97,325

[22] Filed: Nov. 26, 1979

[51] Int. Cl.³ .............................................. A61M 15/06
[52] U.S. Cl. ............................ 128/203.23; 128/204.13; 128/136
[58] Field of Search ....................... 128/203.12, 203.23, 128/203.24, 204.13, 207.14, 136, 205.27, 202.21, 200.24, 203.15; 131/190, 191; 433/91, 93, 140

[56] References Cited
U.S. PATENT DOCUMENTS

| 836,523 | 11/1906 | Moore | 128/203.12 X |
|---|---|---|---|
| 2,669,988 | 2/1954 | Carpenter | 128/136 |
| 3,998,226 | 12/1976 | Harris | 128/203.15 X |
| 4,170,230 | 10/1979 | Nelson | 128/136 X |
| 4,192,309 | 3/1980 | Poulsen | 128/203.15 |

FOREIGN PATENT DOCUMENTS 505545  9/1954  Canada ..................................... 433/140

Primary Examiner—Henry J. Recla

[57] ABSTRACT

A singularly compact inhalator-breathing apparatus is disclosed which fits inside the mouth of a human between the teeth and cheek and functions to controllably mix ambient air with other gases or gas-like material suspensions during the physiological process of inhaling and conveys the inhalant mixture to the rear of the mouth and on to the lungs. The apparatus is capable of transmitting either into or out of the mouth and lungs a flow of air approximate that flow of air which could be expected through normal nasal breathing.

19 Claims, 9 Drawing Figures

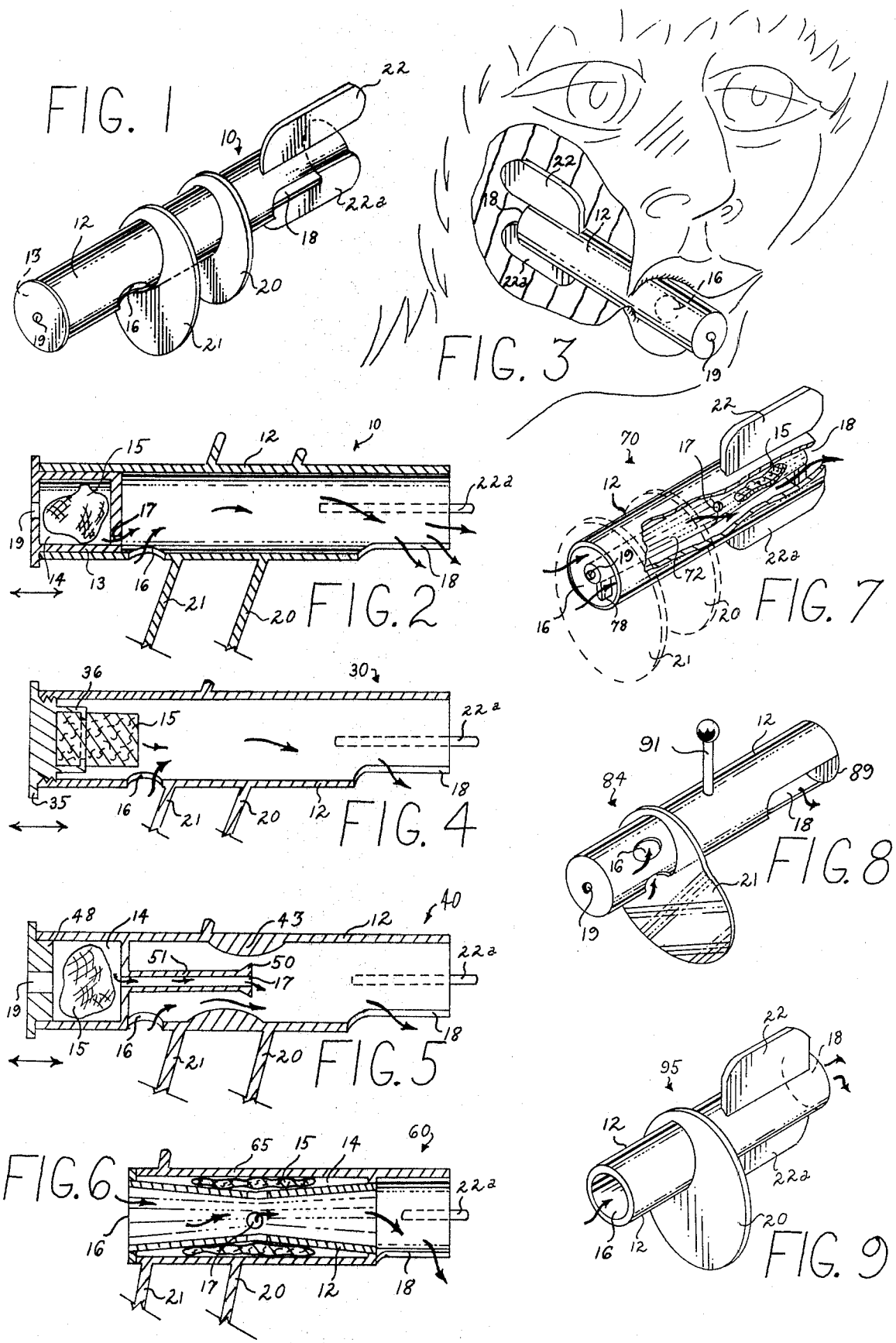

4,261,354

INHALATOR-BREATHING APPARATUS

Application Ser. Nos. 89,035 and 99,855 and 88,043 are related cross references.

BACKGROUND OF THE INVENTION

There are many people who are bothered with a nasal blockage which hinders their breathing, especially at night when they are attempting to sleep. Means are sought by people so afflicted to either promote comfortable mouth breathing by simply avoiding the nasal function with such apparatus as disclosed in Nelson U.S. Pat. No. 4,170,230 or by treating the symptoms of the nasal congestion with nasal sprays, tube inhalators, other various ethical or proprietary drugs in the form of pills, capsules, or liquids, and with mechanical atomizers or steam vaporizers. Except for the mechanical atomizers and steam vaporizers, the above mentioned methods of treating the symptoms of nasal congestion are not entirely satisfactory because these treatments must be intermittently administered in timed dosages with such periodic administration of these medications evidencing the great defect of requiring both a special mental effort and a repetitive physical act on the part of the user of these medicines and methods. Furthermore, experience has shown that the chemically active ingredients of such periodic dosage medications are necessarily strong acting upon first administration and may result in such irritating side effects upon the user as stomachache, sore nasal and throat membranes, and even altered metabolism. Steam vaporizers and mechanical atomizers demand less recurrent physical action or mental effort on the part of the user and deliver the more desirable continuously uniform dosages of mild yet effective medications, but, such devices are not entirely satisfactory since they exhibit the failings of being cumbersome to use, being lacking in portability, and requiring external electrical or gas means to activate them; furthermore, much of the inhalant material is lost and wasted to the surrounding atmosphere thus rendering many of the devices highly inefficient and unacceptable for prescribed dosages of inhalant.

It is therefore an object of this invention to provide an inhalator-breathing apparatus which the user can place inside the mouth that will function to mix ambient air with other gases or gas-like material suspensions during the physiological process of inhaling and to direct this inhalant mixture through the mouth to the lungs without subjecting the mouth to the drying or deleterious effects of an inhalant mixture.

It is another object of this invention while accomplishing the above object, to transmit into the air stream a measureable amount of gas or gas-like material suspension thereby providing for predictable dosages of the inhalant.

It is another object of this invention, while accomplishing the above objects, to convey as required the approximate flow of air into or out of the mouth as would be expected during normal nasal respiration.

It is another object of this invention, while accomplishing the above objects, to minimize the flow of expiring air into or through the contained source of gas or gas-like material suspension, thereby preserving the efficiency of the inhalant source and minimizing the loss of the gas-like material suspension during the process of exhaling.

It is still another object of this invention to accomplish the above objects without requiring special mental effort or repetitive physical action on the part of the user other than such as is irreducibly needed to satisfy immediate respiratory needs.

It is yet another object of this invention to accomplish the above objects with an apparatus which is singularly compact and portable.

THE INVENTION

This invention relates to a compact inhalator-breathing apparatus which fits inside the mouth of a human between teeth and cheek and which apparatus includes: a tube having a constricted interior region; at least one air intake opening in the tube; a container element integral with the tube; the container element is adapted to hold a source of gas or gas-like material suspension. At least one orifice communicates the interior of the integral container element with the interior of the tube; the location of the orifice cooperates with the constricted region of the tube to controllably mix accelerated inhaled air with gas or gas-like material suspension emanating from the integral container through the orifice in the manner of the venturi principle. At least one exhaust opening is adapted to pass the inhalant-air mixture from the tube into the rear of the mouth and on to the lungs. The exhaust opening may be adapted to face at least in part the interior of the mouth. The intake opening with the exhaust opening is sized in combination with the cross-sectional area of the constricted region to provide a flow of air through the tube approximate the flow of air that a human could achieve through normal nasal breathing. Stabilization and positioning of the apparatus in the mouth is enhanced by a fin-like stabilizer situated along part of the length of the tube so that the fin will fit comfortably between the cheek and jaw gum.

As can be seen from the above, the apparatus of this invention, when placed inside the mouth and subjected to the physiological function of inhaling, will mix large quantities of ambient air with continuously controlled small quantities of gas-like material suspension and convey this mixture to the rear of the mouth and into the lungs, thus making it possible for the user to derive from such an inhalant mixture an uninterupted physiological satisfaction without the requirement of special mental effort or repetitive physical action. By routing the air-inhalant mixture to the rear of the mouth the user of this invention avoids exposing his or her mouth to the drying and deleterious effects of an otherwise uncontained air-inhalant passage over and through the several parts of the mouth.

At least one embodiment of the invention additionally provides a sealing element attached to the apparatus. The sealing element extends across the front of the mouth between frontal teeth and lips to an extent of preventing inhaled air from passing through the mouth except through the tube portion of the inhalator-breathing apparatus.

Another embodiment additionally provides for an external stabilizer adapted to fit at least in part accross the front of the mouth external the lips which serves to further enhance the positioning of the device in the mouth and controls the depth into the mouth the device will project.

These and other features of the invention contributing satisfaction in use and economy in manufacture will be more fully understood when taken in connection with the following description and illustrations in which identical numerals refer to identical parts and in which:

FIG. 1 is a perspective view of one embodiment of this invention;

FIG. 2 is a sectional view of the embodiment shown in FIG. 1;

FIG. 3 is a view of a second embodiment of the invention in place in a human mouth showing tube means, fin stabilizer, and integral inhaler means;

FIG. 4 is a sectional view of a third embodiment of this invention;

FIG. 5 is a sectional view of a fourth embodiment of this invention;

FIG. 6 is a sectional view of a fifth embodiment of this invention;

FIG. 7 is a perspective view of a sixth embodiment of this invention with a cut away section showing the inner container element configuration and the air flow path;

FIG. 8 is a perspective view of a seventh embodiment of the invention showing external stabilizing means and rod-like cheek-to-gum stabilizer; and FIG. 9 is a perspective view of an eighth embodiment of the invention showing sealing means and finned stabilizer.

Referring now to the embodiment shown in FIGS. 1 and 2, it can be seen that the breathing apparatus of this invention generally designated by the numeral 10 includes an air flow tube 12 and a container element 13 integral thereto having a cavity 14, therein a source of gas-like material suspension 15. When respirated air enters upstream opening 16, the air is accelerated thereby causing a reduction in air pressure in the vicinity of orifice 17. Orifice 17 communicates with cavity 14 of container element 13. Gaseous material suspension emanating from source 15 exits cavity 14 by way of orifice 17 and combines with the inflowing air to move in the direction of the arrows to exit tube 12 through downstream rear opening 18. Pressure balance port 19 communicates the atmosphere with cavity 14 and allows external air to enter the container element cavity 14 during the inhalation process, however, it is to be understood that in some cases when greater gas flow control is desired, container element 13 may be made without pressure balance port 19, since upon exhalation there will be a reversal of air flow through orifice 17 into cavity 14 thereby reestablishing the pressure potential of cavity 14. The drawings show sealing means 20 which is adapted to fit between the frontal teeth and lips thereby effecting an air seal so that air flows only into or out of tube 12. Sealing means 20 may be flexible or rigid; when sealing means 20 is of a rigid nature it should be made curved to conform to the curvature of the frontal mouth for best results. Affixed to tube means 12 is external stabilizing flange means 21 which prevents swallowing the apparatus thereby promoting comfort and safety to the user in wearing the apparatus. External stabilizing means 21 may also serve to limit the depth into the user's mouth the tube 12 of this invention projects, since external stabilizing means 21 should contact the outer lip area when the apparatus is placed in the mouth. The drawing shows apparatus of this invention 10 having one upstream air opening 16 and one orifice 17, however, there may be a plurality of upstream air openings 16 as when, for instance, these openings are radially oriented about the tube, and there may be a plurality of orifices 17. When there is a plurality of upstream air openings 16, there should be at least one orifice 17 in container element 13 located proximate each upstream air opening 16 for best gas-flow properties. The source of gas-like material suspension 15 may be constructed of cloth-like material or fibrous material, with these materials being saturated with aromatic substances or medicinal powders in the manner well known to those familiar with the inhalator art, or the source 15 may even be a more solid material which evaporates at least in part into gas-like material suspension.

Finned stabilizing means 22, 22a is affixed to the tube means 12 and is adapted for fitment between the cheek and jaw gum so that unwanted rotation or extraneous movement of the apparatus may be minimized. Finned stabilizing means 22, 22a may be of any length or thickness or perimetrical configuration found to be comfortable when the apparatus is in the mouth. Stabilizing means 22, 22a serves the further purpose of insuring that the inhalator-breathing device will not be unwittingly expulsed from the mouth, as might ocurr during sleep, and further serves to prevent the swallowing of the device. Stabilizing means 22, 22a allows for free movement of the jaws and closure of the mouth; it may be rigid or flexible in construction and may be place either on the top or bottom of the tube 12 or in both positions at the same time. Stabilizing means 22, 22a may be situated at any point along the length of tube means 12 so long as some fitment between cheek and gum is retained. In fact, stabilizing means 22, 22a may extend beyond the rear end of the tube means 12 to the extent of defining a spaced area between rearward opening 18 and the fleshy portion of the cheek at the rear of the mouth thereby optimizing free air-flow through a rearward opening 18 to the trachea.

It can be seen in FIG. 2 that container element 13 is removable from tube means 12, thereby allowing for replenishing of the apparatus of this invention with another like element 13 as gas source 15 is used up.

FIG. 3 shows the apparatus of this invention in place in the human mouth. Evident in the drawing is stabilizing means 22, 22a in finned form, tube means 12, and integral inhaler means portion with balance port 19. It is to be understood that any of the methods described in this application for promoting air-gas mixture within tube means 12 would satisfy the general depiction of the invention shown in FIG. 3.

FIG. 4 shows the apparatus of this invention generally designated by the numeral 30, and includes an air flow tube 12, and a source of gas-like material suspension 15. The source of gas-like material suspension 15 is exposed to the inhaled air which passes through upstream opening 16 and directly contacts gas-like material suspension emanating from source 15 wherefrom a mixture of the gas and air moves through tube 12 to exit downstream rear opening 18. Gas source 15 is held in place within the tube by holding element 35 which has retentive node 36 embedded in gas source 15. Gas source 15 with holding element 35 is removable from tube 12 so that source 15 may be replaced as needed. Alternative means for maintaining gas source 15 in place on holding element 35, instead of retentive node 36, could be web-like mesh, with said mesh surrounding source 15 and being attached to holding element 35. The drawing shows sealing means 20 and external lip stabilizer 21, all the attributes of which can be found in the discussion of FIGS. 1, and 2 above about sealing means 20 and stabilizer 21. Finned stabilizing means 22, 22a are shown in phantom.

FIG. 5 shows another embodiment of the breathing apparatus generally designated by the numeral 40. Air enters upstream inlet port 16 and moves along the interior of tube 12 to an area of flow restriction defined by a venturi shaped configuration 43 of the tube 12 wall. Air flow accelerates through venturi shaped configuration 43 thereby causing a reduction in pressure in the vicinity of orifice 17. Gaseous material from cavity 14 emanates from orifice 17 and combines with the accelerated air in the manner of the venturi principle and the air-gas mixture exits tube 12 through downstream opening 18. The source 15 of gaseous material is retained within cavity 14 by removeable retainer means 48. The drawing shows orifice 19 in retainer 48 through which regenerative air may flow into cavity 14; however, such an orifice 19 may not be necessary as exhaled air in tube 12 will regenerate pressure potential in cavity 14 through orifice 17. Flared end 50 of orifice capillary tube 51 serves the purpose of further restricting inhaled air flow through tube 12, thereby bringing about accelerated air flow when inhaling with a resultant drop in pressure in the vicinity of the orifice 17. It is to be understood that any of the well known means for restricting air flow thereby accelerating air flow in tube 12 during inhalation may serve the purpose of this invention; for instance an orifice plate or flow nozzle fashioned in the tube 12 wall would be satisfactory. Likewise, simply flaring the orifice 17 end of capillary tube 51 without utilizing any of the other above mentioned means of accelerating air flow would also suffice. Sealing means 20 and external stabilizer means 21 function as per the discussion for sealing means 20 and stabilizer 21 above. Finned stabilizing means 22, 22a is shown in phantom.

Referring now to FIG. 6, it can be seen in the embodiment generally designated by the numeral 60 how inhaled air enters tube 12 through front opening 16. Tube 12 has a venturi shaped interior configuration with orifices 17 located radially in the wall of tube 12, and proximate the constricted region of the tube 12. There may be instances when one orifice 17 will suffice. Orifices 17 communicate the interior of tube 12 with cavity portion 14 of containing element 65 which coaxially surrounds tube 12. Contained in the cavity portion 14 is source of gaseous matter 15. The resultant drop in pressure in the vicinity of orifices 17 as the air accelerates causes gaseous matter to exit cavity 14 through orifices 17 and enter the air stream within axially disposed tube 12. The mixture of air and gases exits tube 12 through downstream rear opening 18. Sealing means 20 and stabilizer 21 adhere to the discussion of seal 20 and stabilizer 21 above. There may be affixed to the apparatus shown in FIG. 6 stabilizing means 22, 22a which is shown partially in phantom.

FIG. 7 shows another embodiment generally designated by the numeral 70, wherein air flow tube 12 has axially disposed within it container element 72. Inhaled air enters front upstream opening 16 of tube means 12 and is accelerated by means of a restriction in the air flow path defined by the bulbous external configuration of container element 72. Contained within container element 72 is gaseous matter source 15. Located proximate the air flow restriction and communicating the interior of container element 72 with the interior of flow tube 12 is orifice 17, thereby allowing gaseous matter to exit the interior of container element 72, and enter the accelerated air stream with the resultant mixture exiting tube 12 through rear opening 18. Pressure equalizing port 19 communicates the atmosphere with the interior of container element 72, and may not be necessary in some instances when more strident control of gas flow from orifice 17 is indicated. Container element 72 is held in position by holding means 78. Shown in phantom lines are sealing element 20 and external flange stabilizer means 21; the attributes of each are to be found in the discussion of sealing means 20 and stabilizer 21 above. Finned stabilizing means 22, 22a may also be affixed to the embodiment shown in FIG. 7.

FIG. 8 shows an embodiment of this invention generally designated by the numeral 84, wherein air flow tube 12 has radially oriented air openings 16. Air balance port 19 is shown in the end of the tube 12 with the balance port communicating the atmosphere with a gas-source therein. Also shown proximate the closed end 89 of tube 12 is downstream air opening 18 adapted to face the inside of the mouth. External stabilizer means 21 is shown attached to the upstream portion of flow tube 12 and is of a shape to fit comfortably in contact with the exterior of the lips when apparatus 84 is in the mouth. Rod-like stabilizing means 91 is shown affixed to the upper side of the tube means 12; the purpose of rod-like stabilizer is to effect fitment of the apparatus between the cheek and gum.

FIG. 9 shows a last embodiment of the invention generally designated by the numeral 95 and consisting of flow tube 12 with front opening 16 and back opening 18, and sealing means 20. Also shown is stabilizing means 22, 22a.

There may ocurr instances when the user of the apparatus is a patient of extensive mouth surgery whereby the device is removed and replaced often in the mouth; FIG. 8 shows generally a device having no sealing means per se, but only external stabilizing means for use on such occasions. Likewise, it can be seen in FIG. 9 how the apparatus of the invention may be generally constructed without external stabilizer means while still retaining the sealing means for use in some instances of lip injury when an external stabilizer may aggravate the wound. It is to be understood, therefore, that the embodiments shown in FIGS. 1 through 7 may, though with some loss of design efficiency, be constructed in accordance with the generally described embodiments shown in FIGS. 8 and 9 to satisfy either of the two above mentioned needs.

There may ocurr instances when only stabilizer means 22, 22a is necessary in the balance of sealing means 20 and external stabilizer 21. As a matter of fact, the device fits quite comfortably in the mouth and functions satisfactorily under this unique circumstance.

The strength of the air to gas mixture can be predictably controlled by various methods such as: fixing the orifice size in accordance with a known strength of the gas source, compounding the gas source strength in accordance with a known orifice size, varying the orifice location relative to the constricted region in the air flow path, and by constructing the integral container with or without an opening to the atmosphere thereby regulating the amount of pressure in the container relative to the venturi action applied to the orifice, or even constructing the container element with a flexible diaphragm having one side exposed to ambient air pressure and the other side facing the cavity.

The apparatus of this invention may be constructed of any materials known to the medical or dental art, such as latex rubber of plastics which are inert in the human mouth. The invention may be manufactured by means of molding, extrusion, injection molding, casting, etc.

What is claimed:

1. An inhalator-breathing apparatus fitable inside the mouth of a human between cheek and teeth which apparatus comprises: elongated tube means having at least one upstream opening adapted to communicate the interior of said tube means with the atmosphere and at least one downstream opening adapted to communicate said interior of said tube means with the rear poriton of said mouth, said tube means adapted and being of a length sufficient to extend from the front of the mouth back down the side of the mouth to a point adjacent the molars; retainer means disposed integrally within said tube means, a prepared source of gas-like material suspension retained in said tube means by said retainer means so that inhaled air flowing through said tube means will contact at least in part a gas-like material suspension emanating from said prepared source of gas-like material suspension thereby generating an air to gas mixture transferable to said rear portion of said mouth by way of said downstream opening: and stabilizing means affixed to said tube, said stabilizing means being adapted to fit between cheek and jaw gum and contact the jaw gum; said upstream opening and said downstream opening in combination with the cross-sectional area of said tube means being of a size sufficient to allow a flow of air through said tube means approximate to the flow of air said human could achieve through normal nasal breathing.

2. The apparatus of claim 1 wherein said prepared source of gas-like material suspension is fibrous material treated with an aromatic substance.

3. The apparatus of claim 1 wherein said downstream opening is adapted to face at least in part the interior of said mouth.

4. The apparatus of claim 1 wherein there is additionally provided flange stabilizing means attached to said tube means, said flange stabilizing means adapted for fitment externally of the lips.

5. The apparatus of claim 1 wherein said source of gas-like material suspension is removable from said tube means.

6. The apparatus of claim 1 wherein there is additionally provided sealing means affixed to tube means, said sealing means being adapted for fitment at least in part between the frontal teeth and lips.

7. The apparatus of claim 1 wherein said stabilizing means is a fin-like projection from said tube means.

8. The apparatus of claim 1 wherein said stabilizing means is a rod-like projection from said tube means.

9. An inhalator-breathing apparatus fitable inside the mouth of a human between cheek and teeth which apparatus comprises: integral retainer member having a cavity for containing, therein a prepared source of gas-like material suspension; elongated tube means having at least one upstream opening adapted to communicate the interior of said tube means with the atmosphere, and at least one downstream opening adapted to communicate the interior of said tube means with the rear portion of said mouth; said tube means adapted and being of a length sufficient to extend from the front of said mouth down the side of said mouth to a point adjacent the molars; at least one orifice communicating the interior of said tube means with said cavity of said retainer member so that gas-like material suspension contained therein will have access to said interior of said tube means for mixing with inhaled air flowing therethrough, with said mixture exiting said tube means through said downstream opening into the mouth; stabilizing means affixed to said tube means, said stabilizing means being adatped to fit between the cheek and jaw-gum and contact the jaw gum; said upstream opening and said downstream opening in combination with the cross-sectional area of said interior of said tube means being of a size sufficient to allow a flow of air through said tube means approximate to the flow of air said human could achieve through normal nasal breathing.

10. The apparatus of claim 9 wherein said retainer member additionally includes an orifice communicating said cavity of said retainer member with the atmosphere.

11. The apparatus of claim 9 wherein said prepared source of gas-like material suspension is fibrous material treated with an aromatic substance.

12. The apparatus of claim 9 wherein said tube means has a restriction in the air flow path by means of said restriction the inhaled air is accelerated and reduced in pressure; there being located proximate said restriction at least one said orifice communicating said interior of said tube means with said cavity in said retainer member thereby permitting a flow of gas-like material suspension from said cavity into the area of reduced pressure within the interior of said tube means.

13. The provision of claim 12 wherein said restriction is a venturi tube shaped configuration.

14. The apparatus of claim 9 wherein said downstream opening is adapted to face at least in part the interior of said mouth.

15. The apparatus of claim 1 wherein there is additionally provided flange stabilizing means attached to said tube means, said flange stabilizing means being adapted for fitment externally of the lips.

16. The apparatus of claim 9 wherein there is additionally provided sealing means, said sealing means being adapted for fitment at least in part between the frontal teeth and lips.

17. The apparatus of claim 9 wherein said stabilizing means is a fin-like projection from said tube means.

18. The apparatus of claim 9 wherein said stabilizing means is a rod-like projection from said tube means.

19. The apparatus of claim 9 wherein there is additionally provided capillary tube means extending from said orifice in said retainer member to a point proximate said interior of said tube means thereby defining a gas-like material suspension flow path from said cavity of said retainer member to said interior of said tube means.

* * * * *